(12) United States Patent
Atrazhev et al.

(10) Patent No.: US 8,993,270 B2
(45) Date of Patent: *Mar. 31, 2015

(54) SOLID GEL AMPLIFICATION METHOD AND APPARATUS FOR GENOTYPING AND PATHOGEN DETECTION

(75) Inventors: Alexey Atrazhev, Edmonton (CA); Jason Acker, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/809,106

(22) PCT Filed: Jul. 8, 2011

(86) PCT No.: PCT/CA2011/000789
§ 371 (c)(1),
(2), (4) Date: Jan. 8, 2013

(87) PCT Pub. No.: WO2012/003579
PCT Pub. Date: Jan. 12, 2012

(65) Prior Publication Data
US 2013/0149709 A1   Jun. 13, 2013

Related U.S. Application Data

(60) Provisional application No. 61/362,878, filed on Jul. 9, 2010.

(51) Int. Cl.
*C12P 19/34* (2006.01)
*C12Q 1/68* (2006.01)

(52) U.S. Cl.
CPC ............ *C12Q 1/6844* (2013.01); *C12Q 1/6851* (2013.01); *C12Q 1/686* (2013.01)
USPC ........................................................ 435/91.2

(58) Field of Classification Search
USPC ........................................................ 435/91.2
See application file for complete search history.

(56) References Cited

U.S. PATENT DOCUMENTS

| 5,616,478 | A * | 4/1997 | Chetverin et al. ............ 435/91.2 |
| 6,514,768 | B1 | 2/2003 | Guire |
| 2006/0110722 | A1 * | 5/2006 | Beebe et al. ...................... 435/4 |
| 2009/0105082 | A1 * | 4/2009 | Chetverin et al. ................. 506/7 |

FOREIGN PATENT DOCUMENTS

WO   2007111639   10/2007

OTHER PUBLICATIONS

Mitra et al: In Situ Localized Amplification and Contact Replication of Many Individual DNA Molecules; Nucleic Acids Research, 1999, vol. 27, No. 24, e34; p. 1-6.
Strizhkov et al.: PCR Amplification on a Microarray of Gel-Immobilized Oligonucleotides: Detection of Bacterial Toxin- and Drug-Resistant Genes and Their Mutations; Bio Techniques; 29; vol. 29, No. 4(2000); p. 844-857.
Chetverina, Molcular colony diagnostics etc, Biotechniques, Jul. 2002, vol. 33, pp. 154-156 ISSN 0726-6205.

* cited by examiner

*Primary Examiner* — Cynthia B Wilder
(74) *Attorney, Agent, or Firm* — Anthony R. Lambert

(57) ABSTRACT

The present invention provides for a novel system and method for amplification and detection of nucleic acids within a miniaturized device.

24 Claims, 9 Drawing Sheets

Figure 1
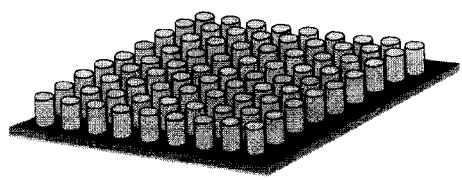 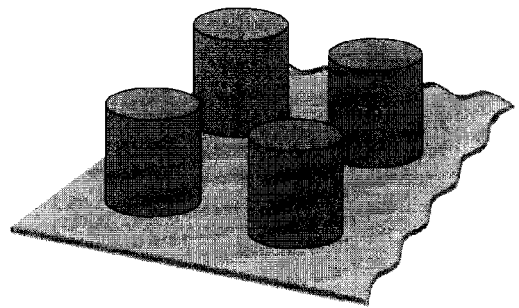
(a) (b)

(a) (b) (c)

Figure 4
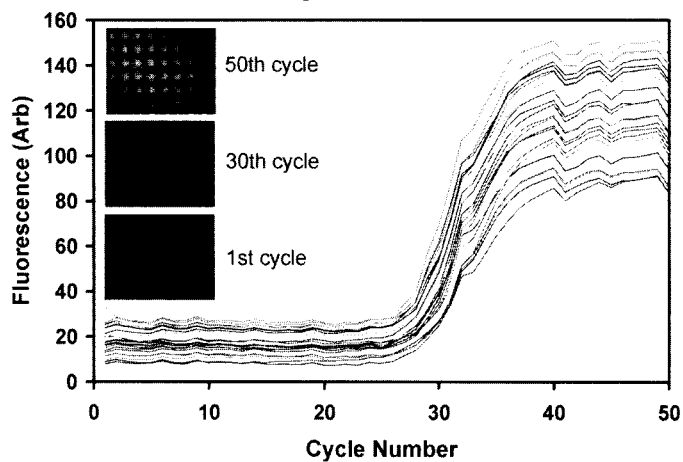
(a)
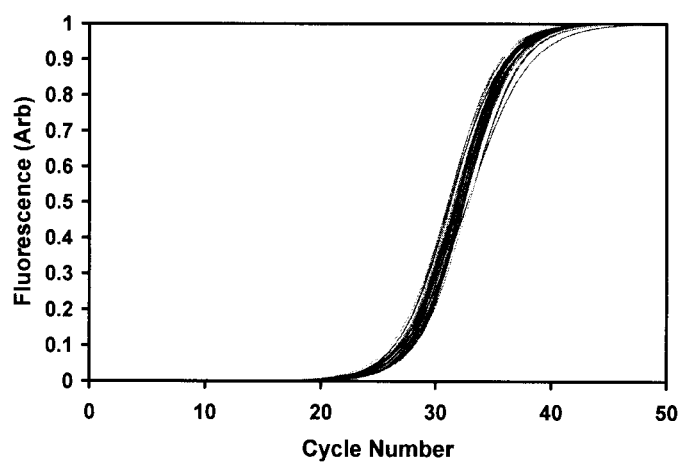
(b)
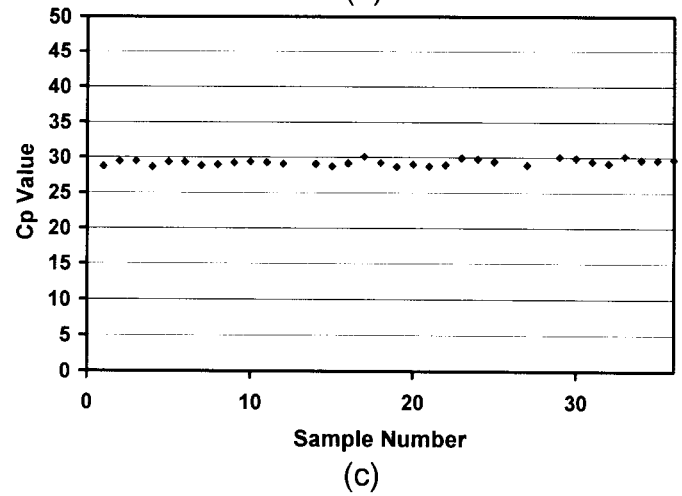
(c)

Figure 5
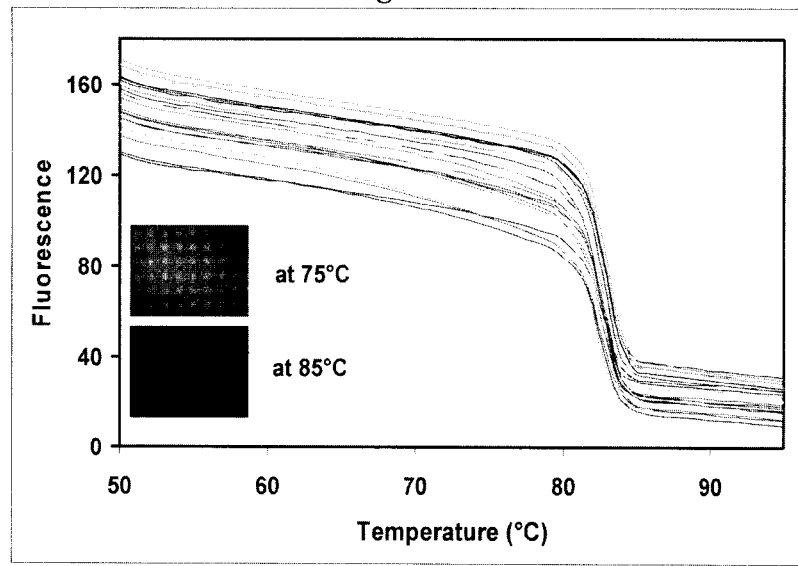
(a)
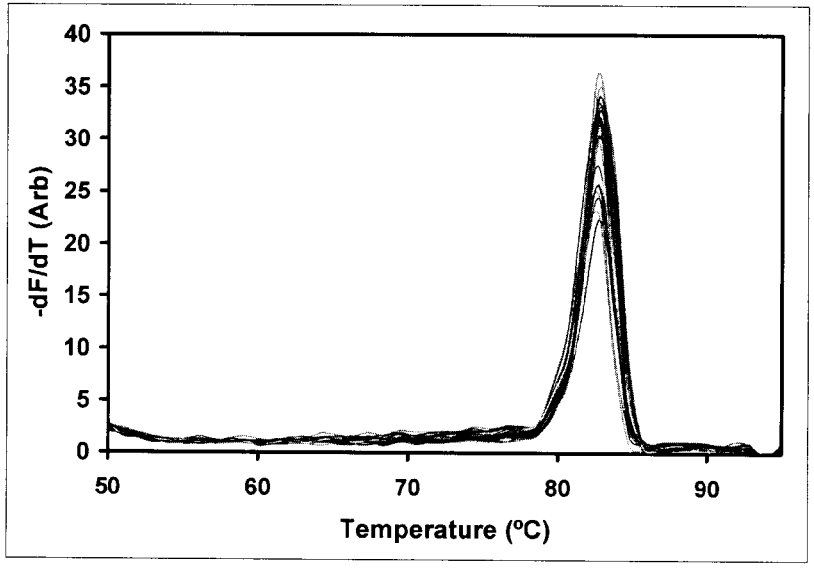
(b)
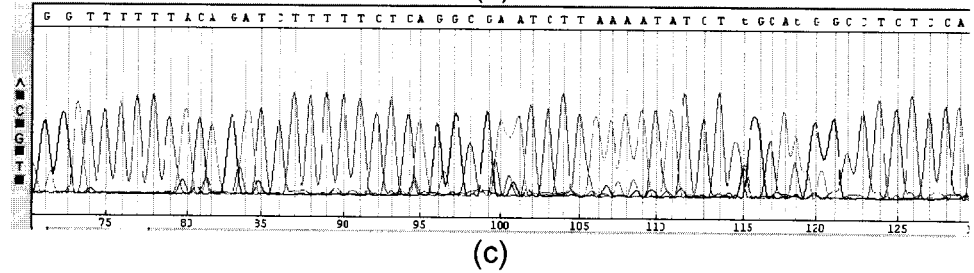
(c)

Figure 6
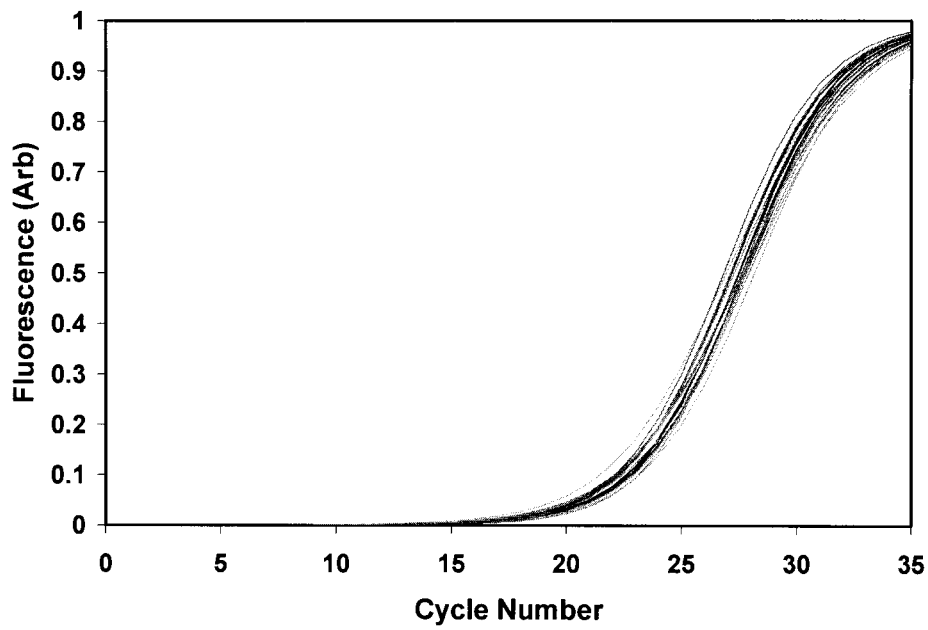
(a)
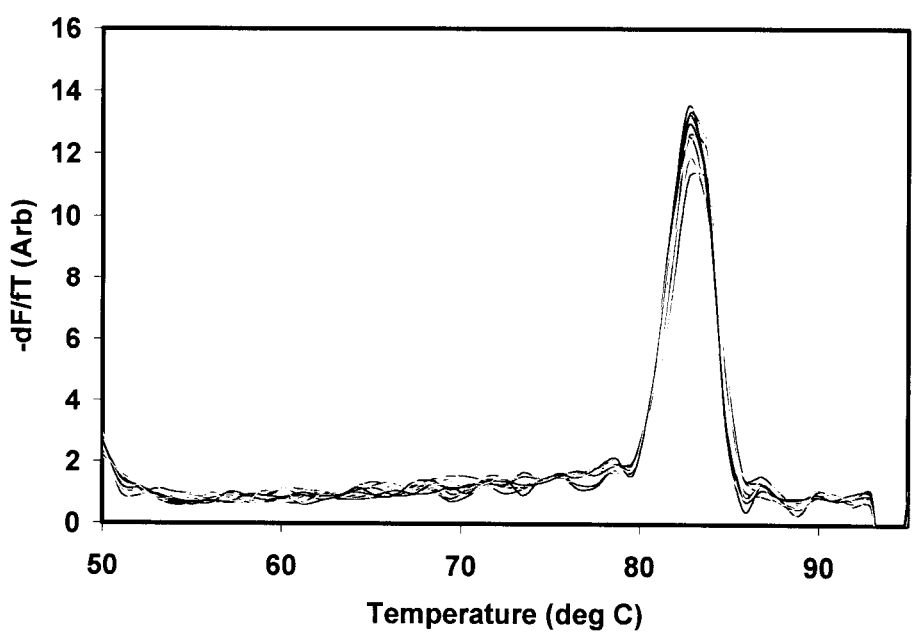
(b)

SEQUENCE LISTING

<160> NUMBER OF SEQ ID NOS: 17

<210> SEQ ID NO 1
<211> LENGTH: 21
<212> TYPE: DNA
<213> ORGANISM: BK virus

<400> SEQUENCE: 1 aaacaccta acctcttcta c                    21

-continued

```
<210> SEQ ID NO 2
<211> LENGTH: 20
<212> TYPE: DNA
<213> ORGANISM: BK virus

<400> SEQUENCE: 2 ttccttttg ctaagtgacc                                                    20

<210> SEQ ID NO 3
<211> LENGTH: 19
<212> TYPE: DNA
<213> ORGANISM: BK virus

<400> SEQUENCE: 3
tattttaaga tccgcctga                                                    19

<210> SEQ ID NO 4
<211> LENGTH: 21
<212> TYPE: DNA
<213> ORGANISM: BK virus

<400> SEQUENCE: 4
gcctgtttac taacagctct g                                                 21

<210> SEQ ID NO 5
<211> LENGTH: 21
<212> TYPE: DNA
<213> ORGANISM: BK virus

<400> SEQUENCE: 5
gcctctttgt aaagctgata g                                                 21

<210> SEQ ID NO 6
<211> LENGTH: 20
<212> TYPE: DNA
<213> ORGANISM: BK virus

<400> SEQUENCE: 6
catgtgacca acacagctac                                                   20

<210> SEQ ID NO 7
<211> LENGTH: 21
<212> TYPE: DNA
<213> ORGANISM: BK virus

<400> SEQUENCE: 7
ctaggtattt tgggactttc a                                                 21

<210> SEQ ID NO 8
<211> LENGTH: 19
<212> TYPE: DNA
<213> ORGANISM: BK virus

<400> SEQUENCE: 8
tgcttatcca gttgagtgc                                                    19

<210> SEQ ID NO 9
<211> LENGTH: 21
<212> TYPE: DNA
<213> ORGANISM: BK virus

<400> SEQUENCE: 9
ccagtcccag gtaatgaata c                                                 21
```

```
<210> SEQ ID NO 10
<211> LENGTH: 21
<212> TYPE: DNA
<213> ORGANISM: BK virus

<400> SEQUENCE: 10
gaattacagg tcaaagtacc c                                             21

<210> SEQ ID NO 11
<211> LENGTH: 18
<212> TYPE: DNA
<213> ORGANISM: BK virus

<400> SEQUENCE: 11
gtgcatgagc atggtgga                                                 18

<210> SEQ ID NO 12
<211> LENGTH: 21
<212> TYPE: DNA
<213> ORGANISM: BK virus

<400> SEQUENCE: 12
aagctaagtg ctgaaaatga c                                             21

<210> SEQ ID NO 13
<211> LENGTH: 18
<212> TYPE: DNA
<213> ORGANISM: BK virus

<400> SEQUENCE: 13
cccaaccaaa agaaaagg                                                 18

<210> SEQ ID NO 14
<211> LENGTH: 16
<212> TYPE: DNA
<213> ORGANISM: Homo sapiens

<400> SEQUENCE: 14
cacagcgagg tgagcc                                                   16

<210> SEQ ID NO 15
<211> LENGTH: 18
<212> TYPE: DNA
<213> ORGANISM: Homo sapiens

<400> SEQUENCE: 15
ctcctgtctt acaggccc                                                 18

<210> SEQ ID NO 16
<211> LENGTH: 26
<212> TYPE: DNA
<213> ORGANISM: Homo sapiens

<400> SEQUENCE: 16
cagaagtttt tgagagtggc atgatg                                        26

<210> SEQ ID NO 17
<211> LENGTH: 28
<212> TYPE: DNA
<213> ORGANISM: Homo sapiens

<400> SEQUENCE: 17
gctgacttct atttatataa cttcaagc                                      28
```

SOLID GEL AMPLIFICATION METHOD AND APPARATUS FOR GENOTYPING AND PATHOGEN DETECTION

CROSS-REFERENCE TO RELATED APPLICATIONS

The present Application claims priority from U.S. Provisional Patent Application No. 61/362,878 filed Jul. 9, 2010 such application is expressly incorporated by reference herein for all purposes.

REFERENCE TO SEQUENCE LISTING

The present Application contains a Sequence Listing which has been submitted electronically in ASCII format via EFS-Web as a file named "13809106_SEQUENCE_LISTING.txt", created on Jan. 9, 2013, and having a size of 3 kilobytes. The sequence listing contained in this ASCII formatted document is herein incorporated by reference in its entirety.

FIELD OF THE INVENTION

The present invention pertains to the field of macro- and microfluidic devices and methods for detection of nucleic acids

BACKGROUND OF THE INVENTION

All of the publications, patents and patent applications cited within this application are herein incorporated by reference in their entirety to the same extent as if the disclosure of each individual publication, patent application or patent was specifically and individually indicated to be incorporated by reference in its entirety.

There is an increasing demand for a small scale array-based and/or microfluidic device that processes micro- or nano-volumes of sample, with time and cost savings arising from miniaturization. Prior art approaches to miniaturised polymerized chain reactions ("PCR") make use of open or enclosed chambers or flow through zones/channel networks with appropriate temperature regulation; some have on-board silicone rubber-based or magnetic-based valving and/or pumping. Although potentially powerful approaches, challenges may arise of pressure seal and/or evaporation, pressure buffering, as well as others such as chemical interference through surface interactions, and evaporation/contamination via the porous, gas permeable membranes used in pumps and valves.

Performing PCR in a colloidal hydrogel matrix (hereafter termed "gel") may confer a multitude of advantages. For example, the DNA, polymerase enzyme and other PCR reagents a) have reduced access to the device materials' surfaces where they may be adsorbed, absorbed, poisoned or otherwise rendered inactive and b) are kept within close proximity to each other without the need for valves or pumps. Likewise, any contaminant solutes from device materials have reduced access to the PCR reaction.

Gels provide a successful medium for PCR, as first introduced by Chetverin et al., see for example U.S. Pat. No. 5,616,478; which is herein incorporated by reference in its entirety. PCR was confined to circular spots in a gel sheet where the initial DNA or RNA templates, formed "molecular polonies" (short for polymerase colonies), named for their similarity to the growth of bacterial colonies in agar; the initial amount of DNA can be accurately estimated by counting the number of polonies. Mitra et al. (Mitra, R. D. et al; *Nucleic Acid Research* 1999, 27, e34) performed DNA amplification in a thin acrylamide film polymerized with all the reagents along with plasmid DNA as their template. In an alternate approach, Strizhkov et al. (Strizhkov, B. N. Et al; *Biotechniques* 2000, 29, 844-857) used nanoliter gel pads to immobilize primers for PCR. Single Nucleotide Polymorphisms (SNPs) in cDNA were detected with polony technology by Butz et al. (Strizhkov, B. N. et al; 2000, 29, 844-857)

Absent the use of immobilized primers within the gel, previous instances of in-gel PCRs were performed in a defined chamber with relatively large volumes (62-65 µL). The present art is in need of a means to perform post PCR analysis of amplicons, such as melting curve analysis ("MCA") without imposing additional steps for the transfer or handling of PCR product and in small volumes normally associated with microfluidic reactions (sub 100 µl).

SUMMARY OF THE INVENTION

The present art has suffered from an inability to perform PCR and MCA within an array of defined spaces of microfluidic volumes absent the immobilizing of at least one of the primers involved in the PCR.

In one aspect, the present invention provides for a method for detecting a nucleic acid molecule, including DNA, cDNA or RNA, within a hydrogel post array comprising providing a hydrogel post array of 2×1 or greater containing a cell-free, enzymatic, nucleic-acid amplification system; applying to at least one of said hydrogel posts nucleic acid molecules, at least one of which may comprise a template for said amplification system; and incubating said hydrogel posts under conditions promoting the synthesis of an amplified nucleic acid product by said amplification system from said at least one template; wherein said amplification system comprises at least two non-immobilized nucleic acids capable of promoting synthesis of amplified nucleic acid product from said template.

In a further aspect, the hydrogel posts contain a fluorescent marker, wherein said fluorescent marker has different fluorescence properties when interacting with double-stranded nucleic acids than with single-stranded nucleic acids and in a still further aspect said fluorescent marker is selected from the group comprising LC Green, SYBR Green and SYTO 62. In further aspect, PCR products can be detected by any agent or characteristic that has a measurable property that differs between forms of nucleic acid, by way of non-limiting example, between single stranded and double stranded nucleic acid.

In another aspect, the hydrogel post is comprised of polyacrylamide of 2.0-3.1% weight per unit volume, and photopolymerized in the absence of APS. In another aspect the polyacrylamide is 2.0-12% weight per volume. In another aspect the template is included in said hydrogel posts. In another aspect the template is provided externally to said hydrogel posts.

In an additional aspect, the present invention provides for a method for detecting a nucleic acid molecule, including DNA, cDNA or RNA, within a hydrogel post array comprising providing a hydrogel post array of 2×1 or greater containing a cell-free, enzymatic, nucleic-acid amplification system; including nucleic acid molecules in at least one of said hydrogel posts, at least one of which may comprise a template for said amplification system; and incubating said hydrogel posts under conditions promoting the synthesis of an amplified nucleic acid product by said amplification system from said at least one template; wherein said amplification system comprises at least two non-immobilized nucleic acids capable of promoting synthesis of amplified nucleic acid product from said template.

In a further aspect, the hydrogel posts contain a fluorescent marker, wherein said fluorescent marker has different fluorescence properties when interacting with double-stranded nucleic acids than with single-stranded nucleic acids and in a still further aspect said fluorescent marker is selected from the group comprising LC Green, SYBR Green and SYTO 62. In further aspect, PCR products can be detected by any agent or characteristic that has a measurable property that differs between forms of nucleic acid, by way of non-limiting example, between single stranded and double stranded nucleic acid In another aspect, the hydrogel post is comprised of polyacrylamide of 2.0-3.1% weight per unit volume, and photopolymerized in the absence of APS. In another aspect the polyacrylamide is 2.0-12% weight per volume. In another aspect the template is included in said hydrogel posts. In another aspect the template is provided externally to said hydrogel posts.

In an additional aspect, the present invention provides for a method for detecting a nucleic acid molecule, including DNA, cDNA or RNA, within a hydrogel post array comprising providing a hydrogel post array of 2×1 or greater containing a cell-free, enzymatic, nucleic-acid amplification system; introducing nucleic acid molecules in a solution in fluid communication with at least one of said hydrogel posts, at least one of which may comprise a template for said amplification system; and incubating said hydrogel posts under conditions promoting the synthesis of an amplified nucleic acid product by said amplification system from said at least one template; wherein said amplification system comprises at least two non-immobilized nucleic acids capable of promoting synthesis of amplified nucleic acid product from said template.

In a further aspect, the hydrogel posts contain a fluorescent marker, wherein said fluorescent marker has different fluorescence properties when interacting with double-stranded nucleic acids than with single-stranded nucleic acids and in a still further aspect said fluorescent marker is selected from the group comprising LC Green, SYR. Green and Styo62. In further aspect, PCR products can be detected by any agent or characteristic that has a measurable property that differs between forms of nucleic acid, by way of non-limiting example, between single stranded and double stranded nucleic acid In another aspect, the hydrogel post is comprised of polyacrylamide of 2.0-3.1% weight per unit volume, and photopolymerized in the absence of APS. In another aspect the polyacrylamide is 2.0-12% weight per volume. In another aspect the template is included in said hydrogel posts. In another aspect the template is provided externally to said hydrogel posts.

The accompanying description illustrates preferred embodiments of the present invention and serves to explain the principles of the present invention

BRIEF DESCRIPTION OF THE FIGURES

FIG. 1 shows a schematic diagram of gel posts of 1 mm diameter and 1.1 mm in height with (a) the 9×9 array of gel posts and (b) an enlarged diagram of four posts in the array;

FIG. 4 shows real-time PCR in gel posts arrays with (a) raw fluorescence data obtained by COD image, (b) processed data as contemplated herein and (c) $C_P$ values obtained for each post;

FIG. 5 shows product detection in gel post arrays using melting point analysis with (a) melting curves of BKV amplicons in gel posts represented in FIG. 4, (b) the negative derivative of fluorescence versus temperature showing the melting point of the PCR product and (c) part of the sequence of the product;

FIG. 6 shows amplification of template exogenous to the gel posts in a 2.8% polyacrylamide gel post array with (a normalized real-time data and (b) melting curves of the BKV amplicons;

DETAILED DESCRIPTION OF THE PRESENT INVENTION

Figure 2:
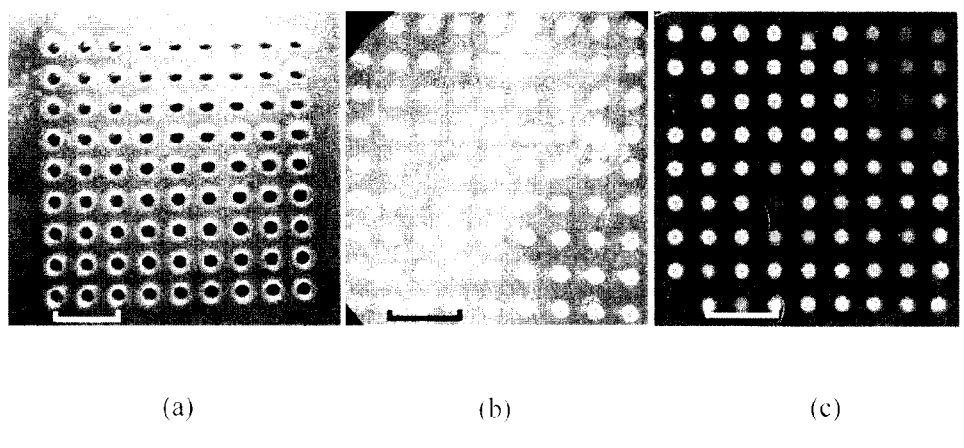
FIG. 2 shows the stages in preparation and use of gel post arrays (a) the mould, (b) 9×9 array of polymerized gel posts, and (c) fluorescent image of the gel posts.

The novel method and system described herein provides for the performance of PCR or other amplification or gene detection method in a gel medium less than 1 μL in volume, obtaining real-time data in situ by detecting the fluorescence of DNA in the presence of an intercalating dye or other means of product or amplicon detection. By performing replicate PCRs in multiple gel posts, statistical data to confirm a result can be obtained. The method of the present invention can be implemented for detection in the same sample of multiple nucleic acids, mutations/polymorphisms contained within a heterogeneous nucleic acid population, or multiple organisms, pathogens, bacteria or viruses within a single sample. As used herein, "post", "posts", "hydrogel post" or "hydrogel posts" refer to any shape or form of a hydrogel such that it is spatially separated from at least one other form of hydrogel. In particular, the present invention contemplates hydrogel forms in the general shape of cylinders, cones, spheres, prisms of any number of sides greater than two, or pyramids of any number of sides greater than two, or portions thereof as well as more amorphous or irregular shapes. The hydrogel posts of the present invention are advantageously of small volumes, less than 100 μl, thereby allowing duplicate reactions within a reduced space and all, advantageously, under the field of view of commercially available cameras or visualizers. The present invention contemplates arrays of any dimension and alignment.

The system described herein is designed to facilitate performance of diagnostic tests in parallel on the same sample, using different posts in the same array. A non-limiting example of the utility of this platform is testing of patients as the patient presents in the clinic, for more rapid results, rather than transport of patient samples to a distant or centralized laboratory. The ability to acquire real-time PCR and MCA using the method and system of the present invention expands the use of this technique to applications such as asymmetric PCR for mutation scanning and genotyping performed with unlabelled probes.

The novel in-gel PCR system of the present invention can perform PCR, melt curve analysis and real time quantitative PCR, with an output that compares favourably with conventional systems representing a "gold standard". Templates from a viral genome and from human genomic DNA are successfully amplified in the gel posts, with BK virus ("BKV"), by way of non-limiting example, readily detected in unprocessed sub-microliter volumes of urine from patients with BK viruria. Further, it is contemplated by the present invention that both processed and unprocessed clinical samples other than urine may be used with the present method and system, including but not limited to, serum, plasma, whole blood, sputum, mucous, aspirates, debrided tissue, scrapings and lymphatic fluid. Further, the present invention is not limited to use with only clinical samples, as the systems and methods described herein may use any sample which may contain a template for the amplification or detection as contemplated herein. The present invention contemplates use of methods for detecting a gene or transcript other than PCR and one skilled in the art would be aware of the variations of PCR and other gene or transcript detection systems.

The present invention provides a method of performing real-time PCR in gels with MCA in an array of cylindrical shaped self-standing gel posts (~0.86 µL per post). In a preferred embodiment the PCR and post-PCR analysis of the resulting amplified nucleic acid (if any) was performed in microfluidic volumes utilizing, in one embodiment, a 9×9 pattern of posts (FIG. 1). An inexpensive prototype heating device with a Peltier element was used for performing PCR and MCA, a diode laser for excitation of fluorescence, and detection optics containing a CCD, all of which controlled by a micro-controller. As well, the present invention provides the novel and desirable performance of in-gel amplification of templates from human genomic DNA ("gDNA") or from cDNA or RNA.

The gel of the present invention is contemplated to hydrophilic polymers forming colloidal hydrogel matrixes which result in similar mobilities of the nucleic acids of sizes contemplated by the present invention as in the specifically described gels herein, by way of non-limiting example, polyacrylamide and polyvinylpyrrolidone ("xPVP") cross-linked with PEG-diacrylate resulting from the photopolymerization of 3.3% vinylpyrrolidone with 0.7% Polyethyleneglycol-diacrylate.

The posts contemplated by the present invention may be cylindrical, spherical, or any other shape and dimension, so long as the posts of the array are physically separated, though they may be in fluid communication or in a common fluid substrate. The size and shape of the posts presented herein are presented as exemplar structures, and it is contemplated that a variety of moulds and therefore post shapes are possible. Also contemplated are inverted shapes placed on a planar surface, for example wells or depressions comprised of a hydrogel. Also contemplated are wells or depressions made within a structure, for example plastic, glass or other materials, filled with hydrogel.

Example 1

Gel Polymerization

The polymerization of acrylamide gel for gel PCR can be initiated either by a photochemical method or by using peroxide. Adding ammonium persulfate (APS) as the initiator peroxide is the widely used method (Sambrook, J. & Russel, D. W.; *Molecular Cloning*, 3rd Edition ed.; CSHL Press, 2001). For photochemical polymerization, 'azobis' (2,2'-azobis(2-methyl-N-(2-hydroxyethyl) propionamide)) or riboflavin is added to the gel mix and the photochemical reaction is started by exposing the gel mix to ultraviolet light. It was noted that the polymerization initiator, APS, inactivated or inhibited the fluorescent dyes such as SYBR Green X and LC Green Plus that are needed for subsequent product detection by MCA, precluding addition of dye prior to the polymerization if the APS is used as the polymerization initiator. To circumvent this problem, gel posts were made by photopolymerizing the PCR reaction mix with LC Green Plus, with or without template DNA, along with the acrylamide gel reagents in a glass mould having a 9×9 array of wells (FIG. 1). An alternate embodiment is to introduce the intercalating dye or other agent after completion of PCR or other amplification reaction. The wells were then sealed with a cover slip treated to promote gel adhesion. Once gel polymerization had occurred, the cover slip was detached from the mould along with the array of gel posts, and immersed in mineral oil to minimize evaporation, as described below.

Example 2

Mould & Cover Slip Preparation

The mould, approximately 20 mm×20 mm, is made with a 1.1 mm thick glass microscope slide permanently bonded to another 1.1 mm thick microscope slide with a 9×9 array of holes as shown in FIG. 2(*a*). FIG. 2(*b*) shows an image of the 9×9 array of polymerized gel posts, while FIG. 2(*c*) shows a fluorescing image of the gel posts. Embodiments incorporating other types of arrays are also possible. Post arrays may be removed from the mould for use as reaction vessels, or in an alternate embodiment may remain within the mould for an enclosed reaction. The scale bar shown in FIG. 2 is 4 mm in length. It is notable that the fluorescence of the gel posts was always uniform throughout any given post, as imaged by CCD; and in particular none of posts show any distinct "polonies". These 2.8% polyacrylamide gels are the softest gels reported for in-gel PCRs. In addition, gel posts are 3D structures with in depth fluorescence that may obscure boundaries of any individual polonies. Each hole is 1 mm in diameter.

To prepare the surface of the mould so that it would not adhere to the gels, a thin layer of Sigma Coat (Sigma, St. Louis, Mo., cat #SL2) was spread onto the surface of the mould and left to dry. The mould was then washed with n-heptane (Applied Bio Systems, Foster City, Calif., cat #400079) and blown dry with air. In contrast, the surface of the cover slips (22 mm×22 mm, Fisher, Fair Lawn, N.J., cat #12-54B) were treated to enhance adherence to the gel by immersing them in a mixture of 40 mL of 95% ethanol, 1 mL of 100% acetic acid (Fluka, Buchs, cat #45725), 8.9 mL of water, 100 µL of 3-(trimethoxysilyl)propyl methacrylate (Sigma, cat #440159) for 1 hour followed by washing with isopropanol (2-propanol). After casting a gel, the mould can be washed and reused for subsequent gel casting or the mould can remain permanently in contact with the gel. In another embodiment, the gel post array may be fully enclosed with a port for introduction of template and/or other reagents.

Example 3

PCR/MCA Process, BKV PCR

The gel can be polymerized with or without template DNA included in the polymerization mixture. In the latter case, the DNA can be added atop the gel posts where it diffuses into the gel before PCR is performed. 100 µL PCR gel mix contained 47 µL PCR reagents, 10 µL gel reagents and 43 µL water. The 47 µL PCR reagents were: 20 µL of 5×PCR buffer (333 mM tris-sulphate, pH 8.6, 83 mM (NH4)2SO4 (Sigma); and 40% sucrose (Sigma)), 4 µL of 50 mM MgCl2 (Fluka), 2 µL of ~10 mM [dNTP] (Sigma), 2 µL of 1% BSA (Sigma), 2 µL of 10 µM primer solution (Integrated DNA technologies, San Diego, Calif.) for each of 2 primers to produce 100 base pair ("bp") product, 2 µL BKV template DNA, 10 µL of 10×LC Green Plus (Idaho Technology Inc., Salt Lake City, Utah) and 3 µL of Taq polymerase (20 units/4). The 10 µL of gel reagents were: 7 µL of a 40% acrylamide (Sigma, cat #A9099)+4% bis-acrylamide aqueous solution (N,N-methylene bisacrylamide, BioRad, Hercules, Calif., cat #BA05-1610201), 2 µL of 3% azobis (Wako, Richmond, cat #VA-086), and 1 µL of 10% TEMED (N,N,N',N'-tetramethylethylenediamine, Sigma, cat #T7024). This mixture was degassed in vacuum and pipetted into the wells in the mould. Once all the wells were full, a 22 mm×22 mm cover slip treated, as noted above, for adherence to the acrylamide was slipped atop the wells. The mould with the cover slip atop was then exposed to the 405 nm laser (~4 mW/cm2 on the posts) for 25 min in order to photo-polymerize the acrylamide mix. The cover slip with the attached posts was then slowly lifted from the mould (FIG. 2(b)), immediately immersed in mineral oil (Sigma, cat #M5904) in a shallow anodized aluminum 23 mm×23 mm pan (posts facing up), and placed on the Peltier element. Thermal cycling was performed with an initial denaturation of 30 s at 94° C. followed by 50 cycles of denaturation at 94° C. for 15 s, annealing at 52° C. for 30 s, and extension at 72° C. for 30 s, and ending with an extension step of 72° C. for 60 s. After completion of PCR, MCA was performed (FIG. 2(c)). To determine the threshold for BKV amplification, BKV PCRs were performed with 34 to 8640 BKV copies/post. Overall, a total of 52/52 independent experiments to amplify BKV were successfully performed on gel posts, confirming reproducibility of the method.

In order to show that PCR can be performed with unprocessed samples, PCR was performed with 1.5 µL of raw urine added to the PCR reaction mix prior to the polymerization. All the PCR parameters are similar to the BKV DNA PCR other than the PCR cycle number was reduced to 35.

For addition of template after polymerization of gel posts, a similar PCR gel mix (as above) was made without BKV DNA and polymerized. After the gel was detached from the mould, a 14 µL BKV template ($2.86 \times 10^7$ copies/mL) was added atop the gel posts and the DNA allowed to diffuse for 30 min in a covered Petri-dish before performing PCR with the same thermal cycle conditions as above. If the DNA added atop the gel was uniformly absorbed, the amount of template DNA was 4900 BKV copies/post. In order to study the size limitation of the product that could be amplified in a given gel concentration, we have also performed BKV PCR (17,280 BKV copies per post) with a series of different primers (Table 1), with the template DNA polymerized in the gels as indicated above.

TABLE 1

Primer sequences for BKV and HPAI amplification by PCR

| Primer description | SEQ ID | Product length (bp) | Sequence |
|---|---|---|---|
| BKV reverse | SEQ ID NO 1 |  | 5'-aaacaccctaacctcttctac-3' |
| BKV forward | SEQ ID NO 2 | 100 | 5'-ttccttttgctaagtgacc-3' |
|  | SEQ ID NO 3 | 150 | 5'-tattttaagatccgcctga-3' |
|  | SEQ ID NO 4 | 200 | 5'-gcctgtttactaacagctctg-3' |
|  | SEQ ID NO 5 | 250 | 5'-gcctctttgtaaagctgatag-3' |
|  | SEQ ID NO 6 | 300 | 5'-catgtgaccaacacagctac-3' |
|  | SEQ ID NO 7 | 350 | 5'-ctaggtattttgggactttca-3' |
|  | SEQ ID NO 8 | 400 | 5'-tgcttatccagttgagtgc-3' |
|  | SEQ ID NO 9 | 450 | 5'-ccagtcccaggtaatgaatac-3' |
|  | SEQ ID NO 10 | 500 | 5'-gaattacaggtcaaagtaccc-3' |
|  | SEQ ID NO 11 | 600 | 5'-gtgcatgagcatggtgga-3' |
|  | SEQ ID NO 12 | 800 | 5'-aagctaagtgctgaaaatgac-3' |
|  | SEQ ID NO13 | 1000 | 5'-cccaaccaaaagaaaagg-3' |
| HPA1 reverse | SEQ ID NO14 |  | 5'-cacagcgaggtgagcc-3' |
| HPA1 forward | SEQ ID NO 15 | 42 | 5'-ctcctgtcttacaggccc-3' |

Example 4

PCR/MCA Process, Genomic DNA PCR

Similar PCRs were performed with purified gDNA added to the gel before or after the polymerization, Overall, gDNA has been successfully amplified in gel posts for 27/27 independent experiments. For the PCR performed with gDNA template polymerized in the gel, a 42 bp product from human HPA 1 (human platelet antigen 1) was amplified. Except for the template and oligonucleotide primers (in Table 1), the PCR reaction mix was similar to that for the BKV PCR. 225 ng of gDNA was added to the 100 µL mix (~2.2 ng per post). PCR thermal cycling conditions were as indicated for the BKV PCR.

For the PCR performed with gDNA added atop the polymerized gel, a 71 bp product from the FGFR2 gene from human gDNA was amplified. Primers used for FGRF2 amplification were forward primer SEQ ID No. 16 (5'

"CAGAAGTTTTTGAGAGTGGCATGATG") and reverse primer SEQ ID NO 17 (5' "GCTGACTTCTATT-TATATAACTTCAAGC"). Fourteen μL of gDNA (30 ng/μL) was pipetted onto the whole array of posts and was left in a covered Petri-dish for 30 min to allow diffusion of gDNA into the gel. If all the gDNA was uniformly absorbed, a DNA concentration of ~5 ng/post is predicted.

Example 5

PCR/MCA Instrumentation

Figure 3:
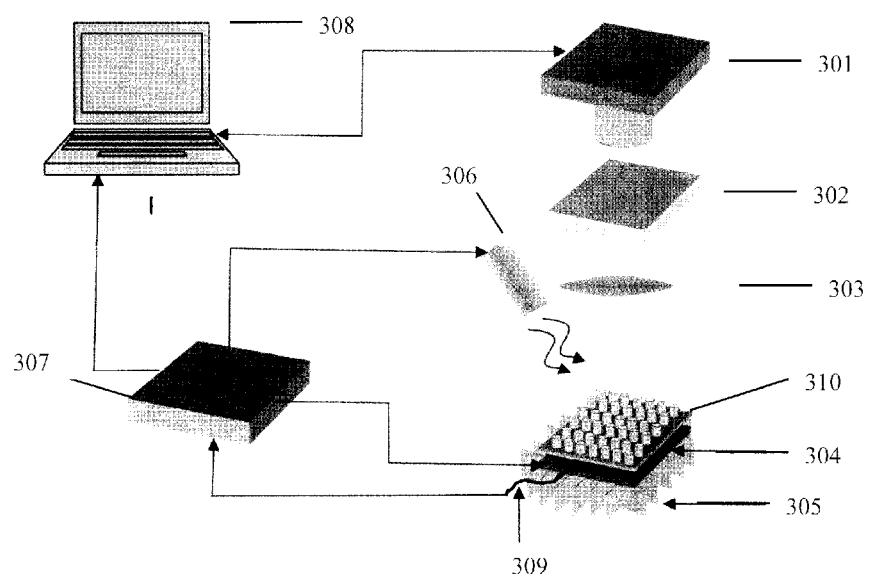
FIG. 3 shows a schematic diagram of the instrument used for performing PCR and MCA.

An inexpensive prototype instrument (shown in FIG. 3) is used to perform the PCR reaction in the gel posts. This instrument uses Motorola 68332 microprocessor 307 to control Peltier element 304 (XLT2398-01L, Marlow Industries, Dallas, Tex.) to perform heating and cooling for PCR and MCA, where Peltier element 304 is placed in thermal communication with hydrogel array 310 and heatsink 305. A charge-coupled device ("CCD") camera 301 (Deep Sky Imager, Meade, Irvine, Calif.) is mounted above Peltier element 304 as well as hydrogel array 310. 65 mW 405 nm laser diode 306 (DL-7146-101S, Sanyo) is mounted at a 70 degree angle to horizontal for a fluorescence excitation source. Laser diode 306 delivers an average of 32 μW of excitation power to each post within hydrogel array 310. 50 nm wide band-pass interference filter centered at 510 nm 302 (BP510/50, Chroma Technology, Bellows Falls, Vt.) is mounted in front of the camera to attenuate excitation light. Biconvex lens 303 (KBX046, Newport, effective focal length 25.4 mm) is mounted between filter 302 and hydrogel array 310. Camera parameters such as the exposure time, light and dark levels are set by the user on PC computer 308, in electronic communication with microprocessor 307. During PCR, once the extension temperature is reached, laser diode 306 is switched on and a fluorescent image of the gel posts is taken by CCD camera 301 and stored by computer 308. During the MCA, laser diode 306 is left on continuously and an image is taken by CCD camera 301 and stored by computer 308 at each degree from 50° C. to 95° C., once the chip has been stabilized at a particular temperature. The system is calibrated by placing calibrated thermocouple 309 (5TC-TT-K-40-36, Omega Engineering Inc., Stamford, Conn.) between the hydrogel posts within hydrogel array 310, under the oil. The settings on the system are then correlated to the observed temperatures of the calibrated thermocouple. Microprocessor 307 is in electronic communication with, and controls, Peltier element 304, temperature sensor 309 and laser diode 306.

Example 6

PCR and Melting Curve Analysis

The CCD images acquired at the extension step of each PCR cycle (total of 50 images) were analysed with ImageJ software (National Institutes of Health, USA) using the MicroArray Plug-in (Dr. Robert Dougherty, OptiNav Inc., Redmond, Wash.) that can be used to plot the cycle number vs. the fluorescence intensity of each post. Even though the mould disclosed herein creates a 9×9 array of posts, optical limitations of the CCD assembly allow image acquisition for only a 6×8 array. In order to determine the efficiency of the PCR, most commercial real-time quantitative PCR instruments embed some proprietary version of data processing in their software. All reported methods characterize the real-time PCR curves by applying curve fitting and determining the threshold values where the fluorescence of the PCR begins to rise above the background signal and the DNA copy numbers can be seen to increase exponentially.

Therefore a sigmoid was fitted to the real-time PCR curves in order to find the exponential region and to find the threshold value, termed the "crossing point" (CP). A Linear Regression of Efficiency or LRE method (Rutledge, R. G. & Stewart, D. BMC *Molecular Biology* 2008, 9) modified with a linear baseline correction (Rebrikov, D. V. & Trofimov, D. Y. *Applied Biochemistry and Microbiology* 2006, 42, 455-463) to fit the sigmoid.

With LRE, the fluorescence of the DNA, $F_c$ at cycle c of the PCR can be written as $$F_c = \frac{F_{Max}}{1 + \left(\frac{F_{Max}}{F_0} - 1\right)(E_{Max} + 1)^{-c}} + F_B + cF_K \qquad \text{Formula 1}$$

where $F_o$, $F_{Max}$, $F_B$ and $F_K$ are the fluorescence values for the initial reaction, endpoint reaction, constant background and variable background, and $E_{Max}$ is the maximum amplification efficiency. A linear baseline to the equation was used to facilitate baseline subtraction with the last two terms of the equation, $F_B$ and $cF_K$. The maximum of the second derivative of the sigmoid is determined to calculate the $C_P$ value, representing the cycle number at which the fluorescence has risen above the background level and the exponential growth of the PCR is at a maximum.

The algorithm of Formula 1, was implemented into computer code using visual basic for applications 6.3 in Microsoft Excel, which receives the fluorescence intensities obtained from the text file output by the ImageJ software and returns multiple plots including the raw, fitted, and normalized data. $C_P$ values for each PCR reaction are also calculated for each post. FIG. 4(a) shows real-time data (experimental data points connected by interpolated lines) for 36 posts that were obtained after PCR performed with 3,456 starting copies of BKV DNA template per post in a 2.8% polyacrylamide gel. Insets in FIG. 4(a) show CCD images of the gel array at the 1$^{st}$ cycle, 30$^{th}$ cycle, and 50$^{th}$ cycle. These results were confirmed in more than 10 independent experiments and no fluorescence above background was detected in the negative controls FIG. 4(b) and FIG. 4(c) show the plots produced by the algorithm and the $C_P$ values for each post respectively.

There is spatial variation in the illumination of the post array due to the oblique incident angle and intentional optical diffusion of the laser. As a result, fluorescence excitation is not uniform on all posts, and thus each real-time PCR curve starts at a different intensity level as seen in FIG. 4(a). These background variations are removed by data processing to produce the normalised curves of FIG. 4(b). Considerable background light between posts is observed, as shown in the inset post array image for the 50th cycle in FIG. 4(a). This background is due to a thin film of gel that remains between the posts as the gel post array is assembled, and where PCR also occurs. One skilled in the art would recognize that modification of assembly protocols would remove or reduce this thin film, and it is contemplated that the present invention also encompasses such modified assembly protocols. Despite the presence of the thin gel layer, fluorescence data is largely independent of the background as they result from the summation of pixels entirely within each post. As disclosed herein, the present invention does not suffer from "cross-talk" between posts.

Melting of the DNA was performed immediately after the PCR was completed. The melting curves were obtained by measuring the fluorescence in the CCD images obtained at each degree from 50° C. to 95° C. as seen in FIG. 5(a). The negative derivative of the fluorescence with respect to the temperature was plotted in FIG. 5(b) and allowed the melting temperature of the PCR products ($T_m$) to be determined as the temperature at the peak 31. The melting temperature for BKV amplicons (average $T_m \pm 1\sigma$ for all 36 traces) was 82.6±0.4° C. The sequence of BKV PCR product was confirmed by sequencing the DNA from one post. Part of the sequence is shown in FIG. 5(c) with sequencing performed with ABI 3130×1 DNA capillary analysis system (Applied Biosystems, Foster City, Calif.). As for the real-time PCR traces in FIG. 4(a), the melting curve baselines of FIG. 5(a) are influenced by the heterogeneous laser illumination; this bias is removed through the data differentiation used to produce FIG. 5(b). Also in keeping with FIG. 4(a), the inset image for 75° C. shows considerable background fluorescence, owing to the thin layer of gel that remains between posts. Insets in (a) show the CCD images of the gel array at 75° C. and 85° C. These results were confirmed in more than 10 independent experiments.

In gel PCR can also be performed using unprocessed clinical samples. The real time PCR curves for the amplification of BKV in unprocessed urine of patients with viruria are shown with real-time data shown in FIG. 6(a) and melting curve analysis is shown in FIG. 6(b). Other embodiments include use of unprocessed blood, saliva, buccal swabs, genital swabs, sputum or other body fluids or tissues.

The results shown in the FIG. 4 and FIG. 5 were acquired with the gels polymerized with the BKV DNA template inside. However, if this technology is to be applied to real-world medical diagnostics, adding clinical samples to the pre-cast gel is likely to be a better approach. PCR with a BKV DNA template that was allowed to diffuse into a pre-cast gel matrix was performed and real-time PCR curves obtained, as shown in FIG. 6(a). This confirms that exogenous template DNA can successfully enter the gel and interact with the embedded PCR components. The melting curve analysis data is shown in FIG. 6(b); for the experiment shown, the average melting temperature was 82.8±0.6° C.

Example 7

Effect of the Gel Concentration on the PCR Product Size

In order to study the limitations of PCR product lengths in polyacrylamide gels, a series of BKV products with lengths from 100 to 1000 bp in 5 different gel concentrations were amplified, with template DNA added prior to polymerization. Table 2 shows PCR amplification of different lengths of BKV template in different polyacrylamide gel concentrations, with a (+) sign indicating that PCR product was detected. Thirteen different primer sets were used to amplify different sized segments of a BKV template, using 5-6 different primer sets per gel post array (see Table 1). Primers were added to the moulds prior to polymerization. Results were confirmed with at least two experiments for each primer set and the sizes of the PCR products were confirmed by running vertical in situ gel electrophoresis on each post. Each array included several different primer sets for distinct sets of gel posts, demonstrating simultaneous multiparameter testing. The results demonstrate that the gel limits the size of the product that can be amplified. As the gel concentration increases, the maximum product size that can be amplified decreases suggesting that the smaller pore size of harder, high concentration gels restricts movement of the larger reagent molecules (DNA template, polymerase etc.) inside the gel as compared to their movement in lower concentration, softer gels.

TABLE 2

BKV template amplification length, gel concentration and cross-talk controls.

| Size of Amplicon (bp) | Concentration of Polyacrylamide | | | | |
|---|---|---|---|---|---|
| | 4% | 6% | 8% | 10% | 12% |
| 100 | + | + | + | + | + |
| 150 | + | + | + | + | + |
| 200 | + | + | + | + | + |
| 250 | + | + | + | + | + |
| 300 | + | + | + | + | + |
| 350 | + | + | + | + | + |
| 400 | + | + | + | + | + |
| 450 | + | + | + | − | − |
| 500 | + | + | − | − | − |
| 550 | + | − | − | − | − |
| 600 | + | − | − | − | − |
| 800 | − | − | − | − | − |
| 1000 | − | − | − | − | − |

In order to show that the primers do not diffuse from one post to another, a separate experiment was performed in which a single primer set was added to some but not all wells prior to the addition of the gel polymerization mix to create a checkerboard of adjacent positive and negative controls. Table 3 shows positive posts have PCR amplification of 100 bp PCR fragment in 6% polyacrylamide gel while negative posts lacked the primer to allow amplification. The lack of amplification observed confirms that cross-talk is suppressed. No product was obtained for posts lacking primers, indicating that cross-contamination by primers does not occur. Diffusion of PCR components between posts was not detected

TABLE 3

Cross-talk controls via checkerboard of alternating positive and negative posts.

| posts with primers (100 bp) | posts without primers |
|---|---|
| + | − |

Example 8

Quantitative PCR

Figure 7:
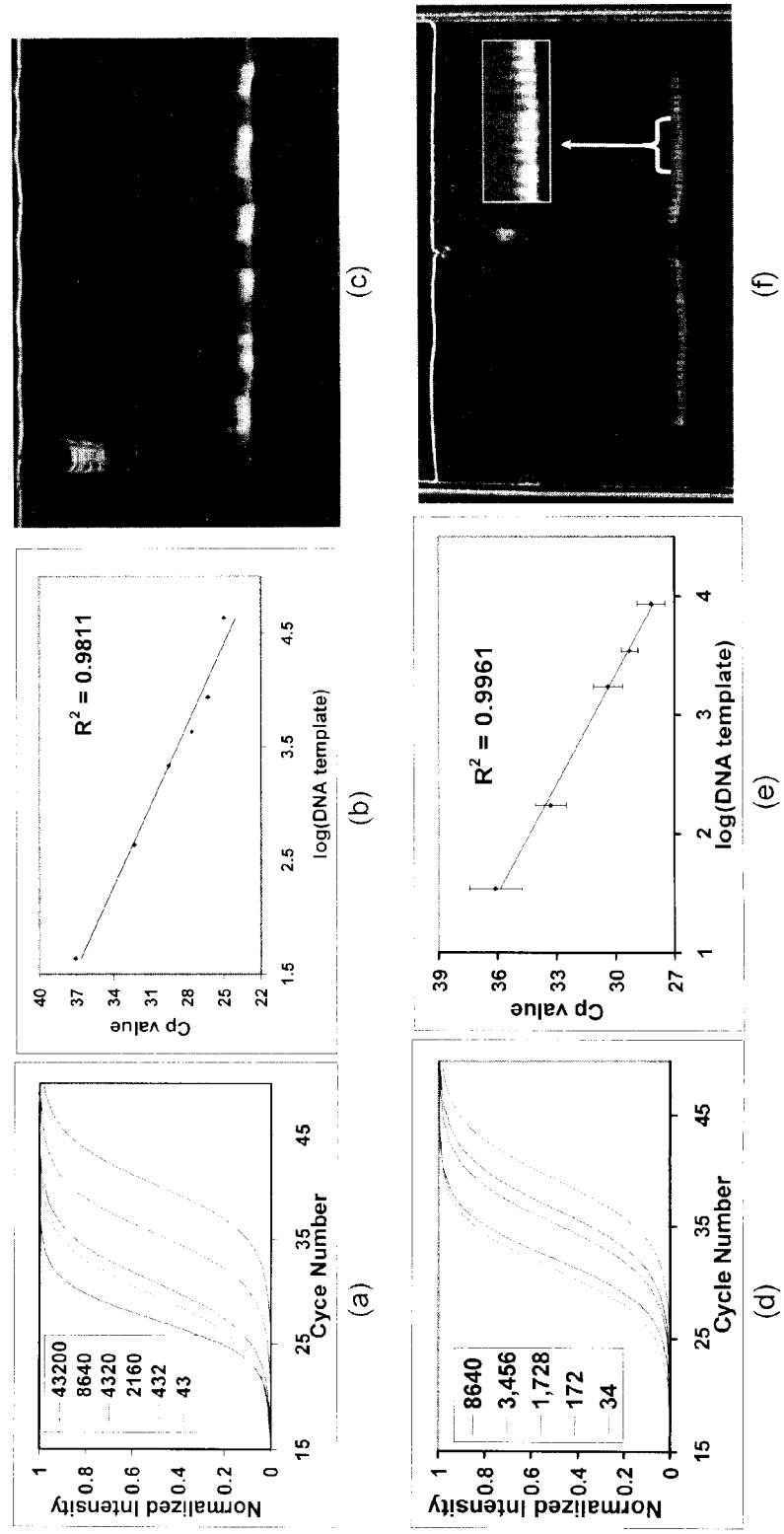
FIG. 7 shows a comparison of BKV DNA PCR in a 2.8% polyacrylamide gels performed in a Lightcycler® (a-c) or gel posts (d-f) in particular (a) Lightcycler® real-time PCR intensity (b) Lightcycler® $C_P$ values versus logarithm of DNA quantity per 0.85 mL reaction, (c) size confirmation of the Lightcycler® amplified products in a vertical polyacrylamide gel, (d) gel post real-time PCR intensity (e) gel post $C_P$ values versus logarithm of DNA quantity per 0.85 μL reaction, (f) size confirmation of the gel post amplified products in a vertical polyacrylamide gel.

In order to characterize quantitative real-time PCR in gel posts, different amounts of BKV DNA were tested under the same PCR conditions to amplify a product of 100 bp in 2.8% polyacrylamide gel posts. For comparison, conventional real-time PCR with the same template was carried out in the Lightcycler®, an instrument that is routinely used for melt curve analysis in clinical diagnostic laboratories and provides a clinically relevant "gold standard". For the Lightcycler® PCR, PCR reaction/gel mixes were polymerized in capillaries in order to mimic the PCR in the gel posts and held a total volume of 0.84 µL per reaction, similar to gel posts. FIG. 7(a-c) shows real-time PCR data generated by the Lightcycler®, relationship of $C_P$ values versus log $[DNA]_{initial}$ and the confirmation of the product size by vertical gel electrophoresis. The analogous results of FIG. 7(d-f) obtained with the in-gel post PCRs mirror those of FIG. 7(a-c) from the Lightcycler®. Each post was picked up individually and placed above the gel before running electrophoresis as shown in FIG. 7(f), with a 100 bp DNA ladder shown in the middle in FIG. 7(f) and on the left in FIG. 7(c). The results below confirm that melt curve analysis of PCR in gel posts matches that from gold standard testing.

FIG. 7(b) and FIG. 7(e) show that, as expected, the $C_P$ values decrease linearly with the logarithm of increasing template DNA copy number for the Lightcycler® and gel post array, respectively, and that the relationship is comparable in the two systems (within ~1 cycle). The melting temperature of the products in the Lightcycler® is 81.5° C. which agrees with the gel posts value of 82.6° C. Both real-time PCR and MCA validate the PCR conditions in gel posts. The inset in FIG. 7(f) is an enlarged section of the gel band, showing individual bands from each gel post. The samples loaded to electrophoresis lanes shown in FIG. 7(f) were from PCR performed with an initial 3456 BKV DNA templates per post.

FIG. 6 shows successful BKV PCR when template was added after the gel was polymerized. Assuming that the DNA was uniformly absorbed by all the 81 posts, each post would have ~4900 copies of BKV template. The Cp value of the PCR shown in FIG. 6(a) is 28.56±0.97, According to the FIG. 7(e) (where template DNA was added prior to the polymerization), the calculated $C_P$ value for a PCR performed with the 4900 copies/post would be 28.86. This calculated value is very similar to the experimental $C_P$ value, 28.56±0.97 that was obtained for the PCR where template DNA was introduced to pre-cast gel posts, confirming that PCR amplification of exogenous DNA template is as efficient as that performed with the template DNA polymerized in the gel. This also indicates that almost all the exogenous DNA placed atop the gel must have diffused into to the gel. The results herein show the feasibility of applying this technique to medical diagnostics where adding clinical sample to pre-cast gel posts is the only feasible approach.

Example 9

Genomic DNA PCR

Figure 8:
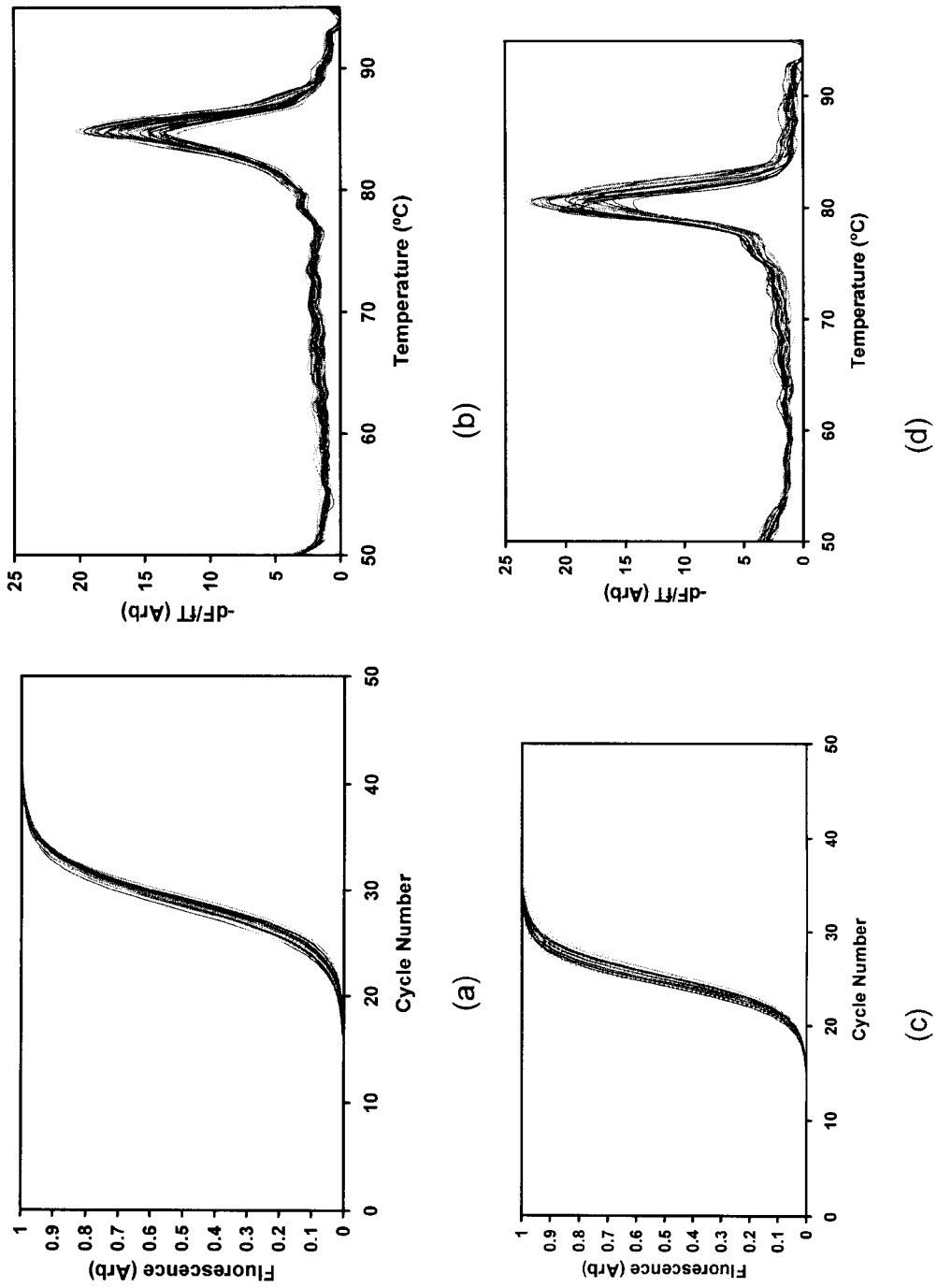
FIG. 8 shows amplification of human genomic DNA by PCR in 2.8% polyacrylamide gel posts with (a) real-time PCR curves for HPA1, (b) melting curve analysis for HPA1, (c) real-time PCR curves for FGFR2 and (d) melting curve analysis for FGFR2.

Human gDNA is made of 3 billion base pairs of DNA, as compared to viral DNA, or plasmid DNAs that are only a few thousand to hundreds of thousands of base pairs in size. During PCR, there is a great deal of heterogeneous non-target DNA present in the long gDNA compared to the uniformity of short plasmid DNA, suggesting that the efficiency of the gDNA PCR is less than that of plasmid DNA. The prior art with respect to gel PCRs used plasmid DNA or cDNA as the template but not gDNA. Two gDNA PCR were undertaken in 2.8% polyacrylamide gel, one with the gDNA polymerized in the gel and one with the gDNA added after polymerization of the gel.

gDNA was subjected to PCR to amplify a 42 bp product containing a known SNP from the human HPA1 gene in the gDNA template polymerized inside the gel, using SEQ ID NOs 14 and 15 as primers; as otherwise shown in Table 1. The template was chosen in anticipation of future genotyping with the gel posts using e.g. allele specific PCR as previously shown. The processed real-time PCR curves and the melting curve analysis data are shown in FIG. 8(a) and FIG. 8(b) respectively, The amount of genomic DNA in the HPA1 PCR is ~2.2 ng per post. PCR was then performed with gDNA template (~5 ng/post) added after the gel polymerization, the gDNA allowed to diffuse into the gel matrix. For the latter approach, the FGFR2 gene from human genomic DNA, with amplification of a 71 bp product also containing a known SNP using SEQ ID NOs 16 and 17 as primers. FIG. 8(c) shows the processed real-time PCR curves while FIG. 8(d) shows the melting curve data for the FGFR2 PCR. Both HPA1 and FGFR2 product sizes were confirmed by vertical gel electrophoresis. This is the first use of gDNA for gel PCR, where gDNA is introduced to the gel mix either prior to or after the polymerization.

Example 10 xPVP Hydrogel

Figure 9:
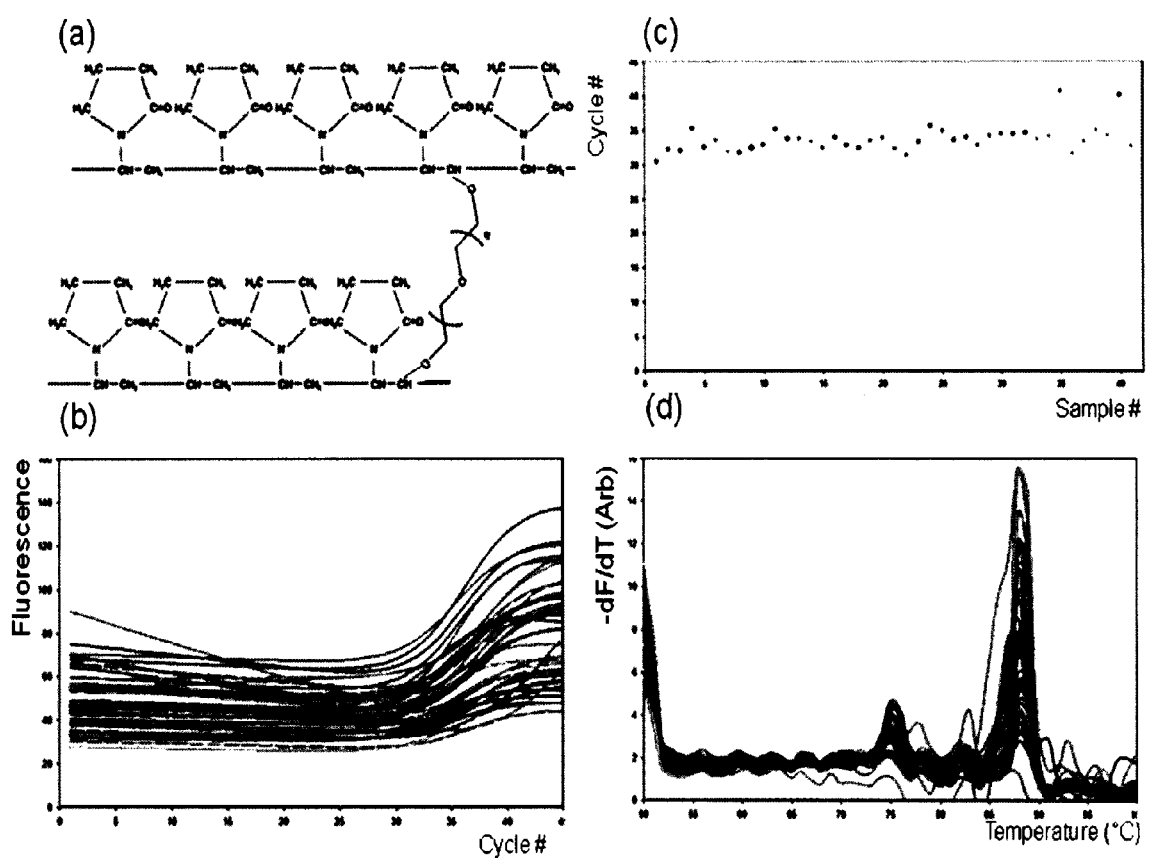
FIG. 9 shows (a) the formula of cross-linked polyvinylpyrrolydone (b), real-time PCR of BKV template in xPVP posts array (c), Cp values and (d) melting point analysis of BKV amplicons by means of negative derivative of fluorescence versus temperature showing the melting point of the PCR product.

A hydrogel other than polyacrylamide, namely crosslinked polyvinylpyrrolidone (xPVP), was used as gel matrix for the posts. It was photo-polymerized with azobis catalysis in the presence of all other ingredients necessary for PCR of BKV template as described in Example 3. The 10 µl of gel reagents contained 33% n-vinylpyrrolydone (Sigma-Aldrich cat #V3409) and 7% of poly(ethylene glycol) diacrylate (Sigma-Aldrich cat #437441) in water. The qPCR and MCA conditions were same as described Example 3. The results are shown on FIG. 9

The prior art has used APS as the polyacrylamide polymerization initiator, precluding the use of in situ real-time detection techniques such as MCA. In contrast, the polymerization initiator used in our photo-polymerization technique, azobis, did not inhibit or inactivate the dye allowing the addition of LC Green Plus dye prior to the polymerization and the acquisition of real-time PCR data at each cycle without disturbing or moving the gel, thus eliminating the need for post PCR staining or the use of expensive and cumbersome hybridization or probe techniques. Alternate dyes are contemplated, including by way of non-limiting example, Styo62 and SYBR Green.

While particular embodiments of the present invention have been described in the foregoing, it is to be understood that other embodiments are possible within the scope of the invention and are intended to be included herein. It will be clear to any person skilled in the art that modifications of and adjustments to this invention, not shown, are possible without departing from the spirit of the invention as demonstrated through the exemplary embodiments. The invention is therefore to be considered limited solely by the scope of the appended claims.

What is claimed is:

1. A method for detecting a nucleic acid molecule within a hydrogel post array comprising
 a) providing an array of hydrogel posts, each hydrogel post containing a respective cell-free, enzymatic, nucleic-acid amplification system, at least one of the respective amplification systems being different from at least another of the respective amplification systems;
 b) applying nucleic acid molecules to at least one of said hydrogel posts, at least one of the nucleic acid molecules comprising a template for said amplification system; and
 c) incubating said hydrogel posts under conditions promoting the synthesis of an amplified nucleic acid product by said amplification system from said at least one template.

2. The method of claim 1 wherein the hydrogel posts contain a marker, wherein said marker has different properties, capable of being measured, when interacting with double-stranded nucleic acids than with single-stranded nucleic acids.

3. The method of claim 2 wherein said measurement is in real-time and the marker is a fluorescent marker.

4. The method of claim 3 wherein said hydrogel post is comprised of polyacrylamide of 2.0-12% weight per unit volume, and photopolymerized in the absence of ammonium persulfate (APS).

5. The method of claim 1 wherein said template is included in said hydrogel posts.

6. The method of claim 1 wherein said template is provided externally to said hydrogel posts.

7. The method of claim 1 wherein the template is between 3,800 and 250,000,000 base pairs in size.

8. A method for detecting a nucleic acid molecule within a hydrogel post array comprising
 a) providing an array of hydrogel posts, each hydrogel post containing a cell-free, enzymatic, nucleic-acid amplification system, at least one of the respective amplification systems being different from at least another of the respective amplification systems;
 b) including nucleic acid molecules in at least one of said hydrogel posts, at least one of which may comprise a template for said amplification system; and
 c) incubating said hydrogel posts under conditions promoting the synthesis of an amplified nucleic acid product by said amplification system from said at least one template.

9. The method of claim 8 wherein the hydrogel posts contain a marker, wherein said marker has different properties, capable of being measured, when interacting with double-stranded nucleic acids than with single-stranded nucleic acids.

10. The method of claim 9 wherein the marker is a fluorescent marker.

11. The method of claim 10 wherein said hydrogel post is comprised of polyacrylamide of 2.0-12% weight per unit volume, and photopolymerized in the absence of ammonium persulfate (APS).

12. The method of claim 8 wherein said template is included in said hydrogel posts.

13. The method of claim 8 wherein said template is provided externally to said hydrogel posts.

14. The method of claim 8 wherein the template is between 3,800 and 250,000,000 base pairs in size.

15. A method for detecting a nucleic acid molecule within a hydrogel post array comprising
 a) providing an array of hydrogel posts, each hydrogel post containing a respective cell-free, enzymatic, nucleic-acid amplification system, at least one of the respective amplification systems being different from at least another of the respective amplification systems;
 b) introducing nucleic acid molecules in a solution in fluid communication with at least one of said hydrogel posts, at least one of which may comprise a template for said amplification system; and
 c) incubating said hydrogel posts under conditions promoting the synthesis of an amplified nucleic acid product by said amplification system from said at least one template.

16. The method of claim 15 wherein the hydrogel posts contain a marker, wherein said marker has different properties, capable of being measured, when interacting with double-stranded nucleic acids than with single-stranded nucleic acids.

17. The method of claim 16 wherein the marker is a fluorescent marker.

18. The method of claim 17 wherein said hydrogel post is comprised of polyacrylamide of 2.0-12% weight per unit volume, and photopolymerized in the absence of ammonium persulfate (APS).

19. The method of claim 15 wherein said template is included in said hydrogel posts.

20. The method of claim 15 wherein said template is provided externally to said hydrogel posts.

21. The method of claim 15 wherein the template is between 3,800 and 250,000,000 base pairs in size.

22. The method of claim 1 wherein said amplification systems comprise at least two non-immobilized nucleic acids, each of the at least two non-immobilized nucleic acids being capable of promoting synthesis of amplified nucleic acid product from said template.

23. The method of claim 8 wherein said amplification systems comprise at least two non-immobilized nucleic acids, each of the at least two non-immobilized nucleic acids capable of promoting synthesis of amplified nucleic acid product from said template.

24. The method of claim 15 wherein said amplification systems comprise at least two non-immobilized nucleic acids, each of the at least two non-immobilized nucleic acids capable of promoting synthesis of amplified nucleic acid product from said template.

* * * * *